(12) United States Patent
Zhao et al.

(10) Patent No.: US 11,249,062 B2
(45) Date of Patent: Feb. 15, 2022

(54) SHALE BRITTLENESS SWEET SPOT EVALUATION METHOD

(71) Applicant: DAGANG OIL FIELD COMPANY OF CNPC, Tianjin (CN)

(72) Inventors: Xianzheng Zhao, Tianjin (CN); Xiugang Pu, Tianjin (CN); Wenzhong Han, Tianjin (CN); Hu Wang, Tianjin (CN); Wei Zhang, Tianjin (CN); Zhannan Shi, Tianjin (CN); Xiongying Dong, Tianjin (CN); Jiapeng Wu, Tianjin (CN)

(73) Assignee: DAGANG OIL FIELD COMPANY OF CNPC, Tianjin (CN)

( * ) Notice: Subject to any disclaimer, the term of this patent is extended or adjusted under 35 U.S.C. 154(b) by 0 days.

(21) Appl. No.: 17/038,574

(22) Filed: Sep. 30, 2020

(65) Prior Publication Data
US 2021/0302403 A1    Sep. 30, 2021

(30) Foreign Application Priority Data

Mar. 27, 2020   (CN) .......................... 202010231435.2

(51) Int. Cl.
*G01N 33/24*   (2006.01)

(52) U.S. Cl.
CPC .................................... *G01N 33/24* (2013.01)

(58) Field of Classification Search
CPC ............................... G01N 33/24; G01V 1/306
See application file for complete search history.

(56) References Cited

U.S. PATENT DOCUMENTS

| | | | | |
|---|---|---|---|---|
| 2011/0282584 A1* | 11/2011 | Baez | ...................... | E21B 49/00 702/13 |
| 2017/0074772 A1* | 3/2017 | Walls | ................... | G01N 23/225 |

(Continued)

FOREIGN PATENT DOCUMENTS

| CN | 105675635 | * | 6/2016 |
|---|---|---|---|
| CN | 106680142 | * | 5/2017 |
| CN | 110715859 | * | 1/2020 |

OTHER PUBLICATIONS

Nur Ali Akbar et al., "An extensive Petrophysical Evaluation for Determining Sweet Spot Intervals in the Ultra-Tight Organic-Rich Shale: A Case Study of the North Sumatra Basin", The 2nd SPWLA Asia Pacific Technical Syposium, Indonesia, 2018.*

(Continued)

*Primary Examiner* — Catherine T. Rastovski
(74) *Attorney, Agent, or Firm* — Calfee Halter & Griswold LLP

(57) ABSTRACT

A shale brittleness sweet spot evaluation method is provided, comprising: determining a brittleness evaluation formula of shale brittleness indexes, shale mineral volume percent content and shale total organic matter mass percent content according to a shale volume-mass conversion formula and a brittleness calculation formula containing shale total organic matter volume percent content and the shale mineral volume percent content; drawing a shale brittleness grading chart of a research area target interval according to the brittleness evaluation formula and measured shale mineral volume percent content values and shale total organic matter mass percent content values of multiple shale samples of the research area target interval; and evaluating shale brittleness sweet spots of the research area target interval. By adopting the method, the shale brittleness sweet spots can be accurately and quantitatively recognized, shale (Continued)

exploration and development cost is reduced, and production capacities of gas-bearing shale formation are increased.

6 Claims, 2 Drawing Sheets

(56) References Cited

U.S. PATENT DOCUMENTS

2018/0094514 A1* 4/2018 Leem ................ E21B 43/26
2018/0188161 A1* 7/2018 Craddock .......... G01N 21/35

OTHER PUBLICATIONS

Yasin et al., "Brittleness Prediction based on Rock's Properties—Application to Sembar shale", Proceedings of the 137th Academic Lecture Meeting of the Physical Exploration Society. 2017.*

Huang et al., "A novel brittleness sweet-spot prediction technology of the tight oil and gas using Seismic Motion Inversion", SEG International Exposition and 87th Annual Meeting, 2017.*

Junping Huang, et at., "A novel brittleness sweet-spot prediction technology of the tight oil and gas using Seismic Motion Inversion." SEG International Exposition and 87th Annual Meeting, pp. 1902-1906.

L. Fernandez Rojas, et al., "Brittleness Analysis: A Methodology to Identify Sweet Spots in Shale Gas Reservoirs," Society of Petroleum Engineers Argentina Exploration and Production of Unconventional Resources Symposium, Buenos Aires, Argentina, Jun. 1-3, 2016.

* cited by examiner

SHALE BRITTLENESS SWEET SPOT EVALUATION METHOD

CROSS REFERENCE TO RELATED APPLICATIONS

This application claims priority to Chinese Application No. 202010231435.2, filed on Mar. 27, 2020, entitled "SHALE BRITTLENESS SWEET SPOT EVALUATION METHOD", which is specifically and entirely incorporated by reference.

FIELD OF THE INVENTION

The present invention relates to the technical field of geological prospecting, and particularly to a shale brittleness sweet spot evaluation method.

BACKGROUND OF THE INVENTION

In the prior art, shale brittleness indexes are mainly evaluated by virtue of a mechanical parameter method or a brittle mineral method. The mechanical parameter method evaluates the shale brittleness indexes based on elastic parameters of rock, i.e. dynamic or static Young modulus and Poisson's ratios. However, single well brittleness evaluation conducted by using the mechanical parameter method requires special logging (e.g. XMAC, cross-dipole array acoustic logging), and data are highly required and are difficult to obtain. Therefore, the brittle mineral method is generally used at present. However, the brittle mineral method is mainly applied to sandstone or carbonate rock, and shale brittleness indexes calculated from the shale are inaccurate.

SUMMARY OF THE INVENTION

Aiming at technical problems that in the prior art, shale brittleness indexes are inaccurately calculated, and shale brittleness sweet spots cannot be accurately recognized, the present invention provides a shale brittleness sweet spot evaluation method. By adopting the method, accurate shale brittleness indexes can be obtained, references are provided for fracturing construction, shale brittleness sweet spots can be favorably found, shale exploration and development cost is reduced, and production capacities of gas-bearing shale formation are increased.

In order to achieve the above-mentioned purposes, the shale brittleness sweet spot evaluation method provided by the present invention comprises the following steps: determining a brittleness evaluation formula of shale brittleness indexes, shale mineral volume percent content and shale total organic matter mass percent content according to a shale volume-mass conversion formula and a brittleness calculation formula containing shale total organic matter volume percent content and the shale mineral volume percent content; drawing a shale brittleness grading chart of a research area target interval according to the brittleness evaluation formula and measured shale mineral volume percent content values and shale total organic matter mass percent content values of multiple shale samples of the research area target interval; and substituting the shale mineral volume percent content values and the shale total organic matter mass percent content values of the shale samples of the research area target interval into the shale brittleness grading chart to obtain shale brittleness grades corresponding to the shale samples so as to evaluate shale brittleness sweet spots of the research area target interval.

Further, wherein the shale volume-mass conversion formula is obtained in ways as follows:

$$\rho_K * V_K = \rho_{rock} * V_{rock}$$

$$V_K = \rho_{rock} * V_{rock} / \rho_K = 2.5 * V_{rock}$$

wherein $\rho_K$ is a kerogen density, $\rho_K = 1.0$ g/cm$^3$; $\rho_{rock}$ is a rock density, $\rho_{rock} = 2.5$ g/cm$^3$; $V_K$ is kerogen volume percent content; $V_{rock}$ is rock volume percent content;

$$V_O = k_0 V_K$$

$$V_O = 2.5 * k_0 V_{rock}$$

wherein $V_O$ is volume percent content of total organic matter; $k_0$ is a conversion coefficient of kerogen converted into organic matter, i.e. the volume of total organic matter is $2.5 * k_0$ times the volume of rock under a same mass, and the shale volume-mass conversion formula is obtained thereout:

$$V_O = 2.5 * k_0 TOC$$

wherein TOC refers to the shale total organic matter mass percent content.

Further, wherein the conversion coefficient $k_0$ of the kerogen converted into the organic matter is 1.3.

Further, wherein the step of determining a brittleness evaluation formula of shale brittleness indexes, shale mineral volume percent content and shale total organic matter mass percent content according to a shale volume-mass conversion formula and the brittleness calculation formula containing the shale total organic matter volume percent content and the shale mineral volume percent content comprises: correcting the shale mineral volume percent content according to the shale total organic matter volume percent content; and substituting the corrected shale mineral volume percent content and the shale volume-mass conversion formula into the brittleness calculation formula containing the shale total organic matter volume percent content and the shale mineral volume percent content, thereby obtaining the brittleness evaluation formula.

Further, wherein the shale mineral volume percent content is corrected in a way as follows:

$$V^*_{mineral} = \frac{V_{mineral}}{V_{qa} + V_{fe} + V_{ca} + V_{do} + V_{an} + V_{cl} + V_o}$$

wherein $V_{mineral}$ is uncorrected shale mineral volume percent content; $V^*_{mineral}$ is corrected shale mineral volume percent content; $V_{qa}$ is uncorrected shale quartz volume percent content; $V_{fe}$ is uncorrected shale feldspar volume percent content; $V_{ca}$ is uncorrected shale calcite volume percent content; $V_{do}$ is uncorrected shale dolomite volume percent content; $V_{an}$ is uncorrected shale analcite volume percent content; $V_{cl}$ is uncorrected shale clay volume percent content; and $V_o$ is the shale total organic matter volume percent content.

Further, wherein the step of drawing a shale brittleness grading chart of a research area target interval according to the brittleness evaluation formula and measured shale mineral volume percent content values and shale total organic matter mass percent content values of multiple shale samples of the research area target interval comprises: simplifying the brittleness evaluation formula to obtain a brittleness simplified formula of the shale brittleness indexes, the shale clay volume percent content and the shale total organic matter mass percent content; and drawing the brittleness grading chart according to the brittleness simplified formula, the shale mineral volume percent content values and the shale total organic matter mass percent content values.

Further, wherein the step of simplifying the brittleness evaluation formula to obtain the brittleness simplified formula of the shale brittleness indexes, the shale clay volume percent content and the shale total organic matter mass percent content comprises: simplifying the brittleness evaluation formula by approximately considering the sum of the volume of quartz, feldspar, calcite, dolomite, analcite, clay and total organic matter in shale as the volume of the shale, thereby obtaining the brittleness simplified formula.

Further, wherein the step of drawing the brittleness grading chart according to the brittleness simplified formula, the shale mineral volume percent content values and the shale total organic matter mass percent content values comprises: drawing a correlation analysis diagram of the shale brittleness indexes and the shale clay volume percent content and a correlation analysis diagram of the shale brittleness indexes and the shale total organic matter mass percent content respectively according to the brittleness simplified formula, the shale total organic matter mass percent content values and the shale clay volume percent content value of the shale mineral volume percent content values; determining a threshold of the shale clay volume percent content and a threshold of the shale total organic matter mass percent content according to the correlation analysis diagram of the shale brittleness indexes and the shale clay volume percent content, the correlation analysis diagram of the shale brittleness indexes and the shale total organic matter mass percent content, and given shale brittleness indexes; determining a relationship curve of the shale total organic matter mass percent content and the shale clay volume percent content according to the given shale brittleness indexes and the brittleness simplified formula; and drawing the brittleness grading chart according to the relationship curve of the shale total organic matter mass percent content and the shale clay volume percent content, the threshold of the shale clay volume percent content and the threshold of the shale total organic matter mass percent content.

Due to technical solutions of the present invention, the present invention at least has the following technical effects:

the shale brittleness sweet spot evaluation method provided by the present invention not only involves influence of mineral components such as feldspar, calcite, dolomite, analcite and clay upon the shale brittleness indexes, but also takes influence of organic matter upon the shale brittleness indexes into account, the shale brittleness indexes can be accurately evaluated, shale brittleness sweet spots are evaluated by drawing the brittleness grading chart, so that the shale brittleness sweet spots can be accurately and quantitatively recognized, the shale exploration and development cost is reduced, and the production capacities of the gas-bearing shale formation are increased.

Other features and advantages of the embodiments of the present invention will be described in detail in subsequent specific embodiments.

DETAILED DESCRIPTION OF THE EMBODIMENTS

The specific embodiments of the present invention will be explained in detail below in conjunction with accompanying drawings. It should be understood that specific embodiments described herein are merely intended to describe and explain the present invention, rather than to limit the present invention.

What needs to be explained is that on the premise of no conflict, embodiments and features of the embodiments of the present invention can be mutually combined.

In the present invention, under a condition of no opposite explanation, used locality nouns such as "up, down, top and bottom" generally refer to directions illustrated in drawings, or are description words for mutual location relationships of components in vertical, perpendicular or gravity directions.

The present invention will be explained in detail below in conjunction with the accompanying drawings and embodiments.

Figure 1:
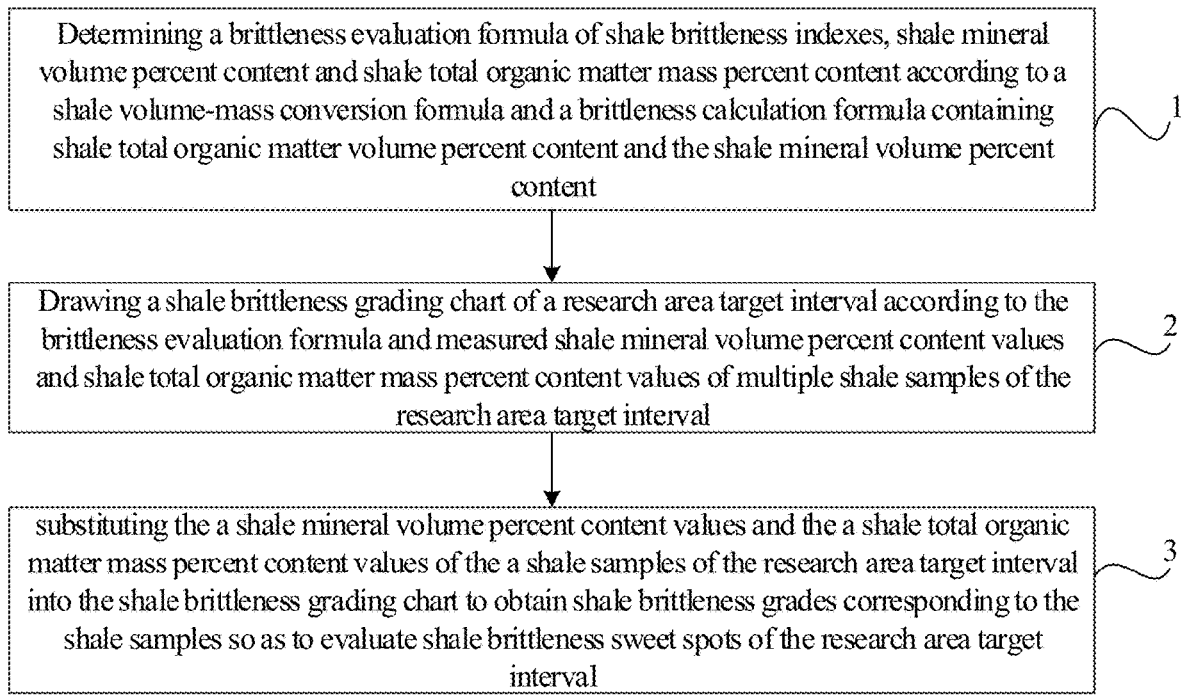
FIG. 1 is a flow diagram of a shale brittleness sweet spot evaluation method according to an embodiment of the present invention.

As shown in FIG. 1, an embodiment of the present invention provides a shale brittleness sweet spot evaluation method, comprising the following steps:

S101: determining a brittleness evaluation formula of shale brittleness indexes, shale mineral volume percent content and shale total organic matter mass percent content according to a shale volume-mass conversion formula and a brittleness calculation formula containing shale total organic matter volume percent content and the shale mineral volume percent content;

S102: drawing a shale brittleness grading chart of a research area target interval according to the brittleness evaluation formula and measured shale mineral volume percent content values and shale total organic matter mass percent content values of multiple shale samples of the research area target interval; and S103: substituting a shale mineral volume percent content value and a shale total organic matter mass percent content value of a shale sample of the research area target interval into the shale brittleness grading chart to obtain a shale brittleness grade corresponding to the shale sample so as to evaluate shale brittleness sweet spots of the research area target interval.

Specifically, in the embodiment of the present invention, the shale total organic matter volume percent content is firstly converted into the shale total organic matter mass percent content in ways as follows:

$$\rho_K * V_K = \rho_{rock} * V_{rock}$$

$$V_K = \rho_{rock} * V_{rock} / \rho_o = 2.5 * V_{rock}$$

wherein $\rho_K$ is a kerogen density, $\rho_K = 1.0$ g/cm$^3$; $\rho_{rock}$ is a rock density, $\rho_{rock} = 2.5$ g/cm$^3$; $V_K$ is kerogen volume percent content; $V_{rock}$ is rock volume percent content.

$$V_O = k_0 V_K$$

$$V_O = 2.5 * k_0 V_{rock}$$

wherein $V_O$ is the volume percent content of total organic matter; and $k_0$ is a conversion coefficient of kerogen converted into organic matter, i.e. the volume of total organic matter is $2.5 * k_0$ times the volume of rock under the same mass:

$$V_O = 2.5 * k_0 TOC$$

wherein TOC refers to the shale total organic matter mass percent content, and the kerogen needs to be further increased by 1.3 times when converted into the organic matter, thereby obtaining the shale volume-mass conversion formula:

$$V_O = 1.3 * 2.5 * TOC = 3.25 TOC$$

Subsequently the shale volume-mass conversion formula is substituted into the brittleness calculation formula containing the shale total organic matter volume percent content and the shale mineral volume percent content:

$$BI = \frac{V_{qa} + V_{fe} + V_{ca} + V_{do} + V_{an}}{V_{qa} + V_{fe} + V_{ca} + V_{do} + V_{an} + V_{cl} + V_o} * 100$$

The brittleness evaluation formula of the shale brittleness indexes, the shale mineral volume percent content and the shale total organic matter mass percent content is determined:

$$BI = \frac{V_{qa} + V_{fe} + V_{ca} + V_{do} + V_{an}}{V_{qa} + V_{fe} + V_{ca} + V_{do} + V_{an} + V_{cl} + 3.25TOC} * 100$$

Wherein BI is brittleness index and $V_{qa}$, $V_{fe}$, $V_{ea}$, $V_{do}$, $V_{an}$ and $V_{cl}$ are respectively the volume percent content of quartz, feldspar, calcite, dolomite, analcite and clay in shale. These data can be obtained by using an X-ray diffraction technology. The shale total organic matter mass percent content can be measured by using a pyrolysis analysis technology. Since $V_O$ is difficult to measure in the prior art, and influence of organic matter upon the shale brittleness indexes is not taken into account either, the shale brittleness indexes are not accurately evaluated. Therefore, by adopting the method of the embodiment of the present invention, the influence of mineral components such as feldspar, calcite, dolomite and analcite and the organic matter upon the shale brittleness indexes is simultaneously taken into account, and the shale brittleness indexes are accurately evaluated.

After the brittleness evaluation formula is obtained, the shale brittleness of each shale sample of multiple shale samples of the research area target interval is sequentially calculated according to the measured shale mineral volume percent content values and shale total organic matter mass percent content values of the multiple shale samples; the shale brittleness grading chart is drawn by virtue of data distribution features and the brittleness evaluation formula for further subdividing the shale brittleness.

Therefore, shale brittleness grade corresponding to a shale sample of the research area target interval can be obtained by substituting the shale mineral volume percent content value and the shale total organic matter mass percent content value of the shale sample into the drawn shale brittleness grading chart for evaluating the shale brittleness sweet spot.

The method provided by the present invention involves the influence of the mineral components such as quartz, feldspar, calcite, dolomite, analcite and clay upon the shale brittleness indexes, and takes the influence of the organic matter upon the shale brittleness indexes into account as well, the shale brittleness indexes can be accurately evaluated, the shale brittleness sweet spots are quantitatively evaluated by drawing the brittleness grading chart, so that the shale brittleness sweet spots can be accurately and quantitatively recognized, shale exploration and development cost is reduced, and production capacities of gas-bearing shale formation are increased.

Further, the step of determining the brittleness evaluation formula of the shale brittleness indexes, the shale mineral volume percent content and the shale total organic matter mass percent content according to the shale volume-mass conversion formula and the brittleness calculation formula containing the shale total organic matter volume percent content and the shale mineral volume percent content comprises: correcting the shale mineral volume percent content according to the shale total organic matter volume percent content; and substituting the corrected shale mineral volume percent content and the shale volume-mass conversion formula into the brittleness calculation formula containing the shale total organic matter volume percent content and the shale mineral volume percent content, thereby obtaining the brittleness evaluation formula.

Specifically, in the embodiment of the present invention, since the shale mineral volume percent content detected by using the X-ray diffraction technology does not take the shale total organic matter volume percent content into account, the shale total organic matter volume percent content needs to be taken into account to correct the shale mineral volume percent content after the shale total organic matter volume percent content is determined.

Further, the shale mineral volume percent content is corrected in a way as follows:

$$V^*_{mineral} = \frac{V_{mineral}}{V_{qa} + V_{fe} + V_{ca} + V_{do} + V_{an} + V_{cl} + V_o}$$

wherein $V_{mineral}$ is uncorrected shale mineral volume percent content; $V^*_{mineral}$ is corrected shale mineral volume percent content; $V_{qa}$ is uncorrected shale quartz volume percent content; $V_{fe}$ is uncorrected shale feldspar volume percent content; $V_{ca}$ is uncorrected shale calcite volume percent content; $V_{do}$ is uncorrected shale dolomite volume percent content; $V_{an}$ is uncorrected shale analcite volume percent content; $V_{cl}$ is uncorrected shale clay volume percent content; and $V_o$ is the shale total organic matter volume percent content.

For example, shale quartz volume percent content can be corrected in the way mentioned above:

$$V^*_{qa} = \frac{V_{qa}}{V_{qa} + V_{fe} + V_{ca} + V_{do} + V_{an} + V_{cl} + V_o}$$

wherein $V_{qa}^*$ is corrected shale quartz volume percent content. Corrected shale feldspar volume percent content $V_{fe}^*$, corrected shale calcite volume percent content $V_{ca}^*$, corrected shale dolomite volume percent content $V_{do}^*$, corrected shale analcite volume percent content $V_{an}^*$ and shale clay volume percent content $V_{cl}^*$ can also be corrected in the same way.

Subsequently, the corrected shale mineral volume percent content and the shale volume-mass conversion formula are substituted into the brittleness calculation formula containing the shale total organic matter volume percent content and the shale mineral volume percent content, thereby obtaining a corrected brittleness evaluation formula:

$$BI = \frac{V^*_{qa} + V^*_{fe} + V^*_{ca} + V^*_{do} + V^*_{an}}{V^*_{qa} + V^*_{fe} + V^*_{ca} + V^*_{do} + V^*_{an} + V^*_{cl} + 3.25TOC} * 100$$

According to the method provided by the present invention, the mineral volume percent content is corrected, so that precision of the shale brittleness indexes can be improved, the shale brittleness sweet spots can be favorably evaluated, fracturing construction schemes can be instructed, and fracturing effects and exploration capacities of the shale can be improved.

Further, the step of drawing the shale brittleness grading chart of the research area target interval according to the brittleness evaluation formula and the measured shale mineral volume percent content values and the shale total organic matter mass percent content values of the multiple shale samples of the research area target interval comprises: simplifying the brittleness evaluation formula to obtain a brittleness simplified formula of the shale brittleness indexes, the shale clay volume percent content and the shale total organic matter mass percent content; and drawing the brittleness grading chart according to the brittleness simplified formula, the shale mineral volume percent content values and the shale total organic matter mass percent content values.

Specifically, the brittleness evaluation formula contains the volume percent content of quartz, feldspar, calcite, dolomite, analcite and clay. However, the content of as many as 6 minerals cannot be accurately calculated only by virtue of logging data yet, and thus wide application of the brittleness evaluation formula is limited. Therefore, the brittleness evaluation formula requires to be simplified so as to obtain the brittleness simplified formula, and the brittleness grading chart is drawn according to the brittleness simplified formula, the shale mineral volume percent content values and the shale total organic matter mass percent content values.

Further, the step of simplifying the brittleness evaluation formula to obtain the brittleness simplified formula of the shale brittleness indexes, the shale clay volume percent content and the shale total organic matter mass percent content comprises: simplifying the brittleness evaluation formula by approximately considering the sum of the volumes of quartz, feldspar, calcite, dolomite, analcite, clay and total organic matter in the shale as the volume of shale, thereby obtaining the brittleness simplified formula.

Specifically, the volume of other impurities in the shale are small and can be ignored, so that in the embodiment of the present invention, the sum of the volumes of quartz, feldspar, calcite, dolomite, analcite, clay and total organic matter in the shale can be approximately considered as the volume of the shale. The brittleness evaluation formula is simplified as follows by taking denominator
$V_{qa}^{*}+V_{fe}^{*}+V_{ca}^{*}+V_{do}^{*}+V_{an}^{*}+V_{cl}^{*}+3.25TOC$ in the brittleness evaluation formula as 100:

$$BI = \frac{100 - V_{cl}^{*} - 3.25TOC}{100} * 100$$

thereby obtaining the brittleness simplified formula of the shale brittleness indexes, the shale clay volume percent content and the shale total organic matter mass percent content:

$$BI = 100 - V_{cl}^{*} - 3.25TOC$$

Therefore, only two parameters, i.e. the shale clay volume percent content and the shale total organic matter mass percent content, need to be calculated by virtue of logging. A shale total organic matter mass percent content calculation method is relatively mature and high in accuracy, the shale clay volume percent content is mainly determined by establishing a statistical relationship between core experiment data and logging data, an interpretation model established with abundant core data is often relatively high in precision, and the simplified shale brittleness indexes are basically identical to shale brittleness indexes before simplification.

According to the method provided by the present invention, on the premise of ensuring calculation precision, the calculation formula of the shale brittleness indexes is simplified, and calculation difficulties are reduced.

Further, the step of drawing the brittleness grading chart according to the brittleness simplified formula, the shale mineral volume percent content values and the shale total organic matter mass percent content values comprises: drawing a correlation analysis diagram of the shale brittleness indexes and the shale clay volume percent content and a correlation analysis diagram of the shale brittleness indexes and the shale total organic matter mass percent content respectively according to the brittleness simplified formula, the shale total organic matter mass percent content values and the shale clay volume percent content value of the shale mineral volume percent content values; determining a threshold of the shale clay volume percent content and a threshold of the shale total organic matter mass percent content according to the correlation analysis diagram of the shale brittleness indexes and the shale clay volume percent content, the correlation analysis diagram of the shale brittleness indexes and the shale total organic matter mass percent content and given shale brittleness indexes; determining a relationship curve of the shale total organic matter mass percent content and the shale clay volume percent content according to the given shale brittleness indexes and the brittleness simplified formula; and drawing the shale brittleness grading chart according to the relationship curve of the shale total organic matter mass percent content and the shale clay volume percent content, the threshold of the shale clay volume percent content and the threshold of the shale total organic matter mass percent content.

Specifically, in the embodiment, multiple shale samples are firstly collected from the research area target interval. The shale clay volume percent content of each sample is detected by using an X-ray diffraction technology, the shale total organic matter mass percent content of each sample is detected by using a pyrolysis analysis technology, and the shale brittleness indexes of each sample are calculated by virtue of the brittleness simplified formula. Then, the correlation analysis diagram of the shale brittleness indexes and the shale total organic matter mass percent content is drawn by taking the shale total organic matter mass percent content as an abscissa and the shale brittleness index as an ordinate. The correlation analysis diagram of the shale brittleness indexes and the shale clay volume percent content is drawn by taking the shale clay volume percent content as an abscissa and the shale brittleness index as an ordinate. The relationship between the shale total organic matter mass percent content and the shale brittleness indexes and the relationship between the shale clay volume percent content and the shale brittleness indexes are determined according to artificially given brittleness boundary values $Y_1$ and $Y_2$ of low brittleness, medium brittleness and high brittleness in the correlation analysis diagrams by virtue of data distribution features, and the threshold of the shale clay volume percent content and the threshold of the shale total organic matter mass percent content are determined. Relationship curves of the shale total organic matter mass percent content and the shale clay volume percent content are determined, and a curve 1 is obtained by virtue of $BI=Y_1$:

$$100-Y_1=V_{cl}*+3.25TOC$$

A curve 2 is obtained by virtue of BI=$Y_2$:

$$100-Y_2=V_{cl}*+3.25TOC$$

Subsequently, a chart is established by taking the shale total organic matter mass percent content as an abscissa and the shale clay volume percent content as an ordinate. The curve 1 and the curve 2 are marked in the chart, the chart is divided in combination with the threshold of the shale clay volume percent content with the threshold of the shale total organic matter mass percent content, thereby obtaining the shale brittleness grading chart of the research area target interval.

By adopting the method provided by the present invention, the shale brittleness sweet spots can be more visibly and quantitatively represented. By substituting the shale mineral volume percent content value and the shale total organic matter mass percent content value of a shale sample of the research area target interval into the shale brittleness grading chart to obtain the shale brittleness grade corresponding to the shale sample, the shale brittleness can be evaluated, so that the shale brittleness sweet spots can be found conveniently.

Embodiment 1

Shale in a well A of an oil field in the Bohai Bay Basin is subjected to experimental analysis. Burial depths of samples are 2925-3298 m. The volume percent content of main minerals such as quartz, feldspar, analcite, calcite, dolomite and clay in each shale sample is respectively measured by using the X-ray diffraction technology. The shale total organic matter mass percent content of each shale sample is measured by using the pyrolysis analysis technology. Average values of shale mineral volume percent content and average values of shale total organic matter mass percent content at the same burial depths are shown in a Table 1 as follows:

TABLE 1

Mechanical and Mineralogical Analysis Statistic Table of Shale in Well A of Oil Field in Bohai Bay Basin

| Depth (m) | XRD Mineral Component Volume Percent Content (%) | | | | | | TOC (%) |
|---|---|---|---|---|---|---|---|
| | Quartz | Feldspar | Analcite | Calcite | Dolomite | Clay | |
| 2925.5 | 18 | 15 | 17 | 21 | 12 | 15 | 0.59 |
| 2937.6 | 15 | 18 | 24 | 19 | 7 | 16 | 7.24 |
| 2955.5 | 16 | 21 | 2 | 5 | 8 | 14 | 5.51 |
| 2966.0 | 14 | 12 | 9 | 1 | 39 | 7 | 3.60 |
| 2974.0 | 10 | 7 | 14 | 5 | 52 | 11 | 3.74 |
| 2999.4 | 29 | 55 | 0 | 9 | 0 | 4 | 2.09 |
| 3012.5 | 22 | 15 | 44 | 3 | 0 | 15 | 0.23 |
| 3025.1 | 17 | 28 | 24 | 13 | 6 | 11 | 3.10 |
| 3032.0 | 16 | 15 | 14 | 14 | 28 | 12 | 2.43 |
| 3032.2 | 14 | 11 | 16 | 5 | 43 | 10 | 2.43 |
| 3073.8 | 15 | 14 | 17 | 3 | 31 | 19 | 4.34 |
| 3187.2 | 15 | 26 | 6 | 6 | 26 | 20 | 5.47 |
| 3197.1 | 21 | 18 | 6 | 8 | 18 | 20 | 0.78 |
| 3209.0 | 18 | 38 | 0 | 7 | 11 | 25 | 9.27 |
| 3281.2 | 18 | 21 | 27 | 6 | 0 | 27 | 0.87 |
| 3288.2 | 16 | 13 | 14 | 17 | 21 | 18 | 0.25 |
| 3297.8 | 14 | 9 | 8 | 10 | 48 | 10 | 4.71 |

The measured shale clay volume percent content and shale total organic matter mass percent content are substituted into the brittleness simplified formula to calculate the shale brittleness index of each shale sample. The correlation analysis diagram of the shale brittleness indexes and the shale total organic matter mass percent content is drawn by taking the shale total organic matter mass percent content as the abscissa and the shale brittleness index as the ordinate, and corresponding marking is conducted in the correlation analysis diagram according to the shale brittleness index and the shale total organic matter mass percent content of each shale sample. The correlation analysis diagram of the shale brittleness indexes and the shale clay volume percent content is drawn by taking the shale clay volume percent content as the abscissa and the shale brittleness index as the ordinate, and corresponding marking is conducted in the correlation analysis diagram according to the shale brittleness index and the shale clay volume percent content of each shale sample.

$Y_1$=60 and $Y_2$=80 are artificially given, the relationship between the shale total organic matter mass percent content and the shale brittleness indexes and the relationship between the shale clay volume percent content and the shale brittleness indexes are determined by virtue of data distribution features: the higher the TOC and $V_{cl}*$ are, the lower the brittleness index (BI) is; when $V_{cl}*$ is smaller than 20%, BI of most shale samples is greater than 80%, so the shale is high-brittleness shale; and when TOC is greater than 6% or $V_{cl}*$ is greater than 40%, BI of the shale samples is smaller than 60%, so the shale is low-brittleness shale. Therefore, it can be concluded that the threshold of the TOC is 6% and the threshold of the $V_{cl}*$ is 20% and 40%.

$Y_1$=60 is substituted into the brittleness simplified formula so as to obtain the curve 1.

$$40=V_{cl}*+3.25TOC$$

$Y_{2=80}$ is substituted into the brittleness simplified formula so as to obtain the curve 2:

$$20=V_{cl}*+3.25TOC$$

Figure 2:
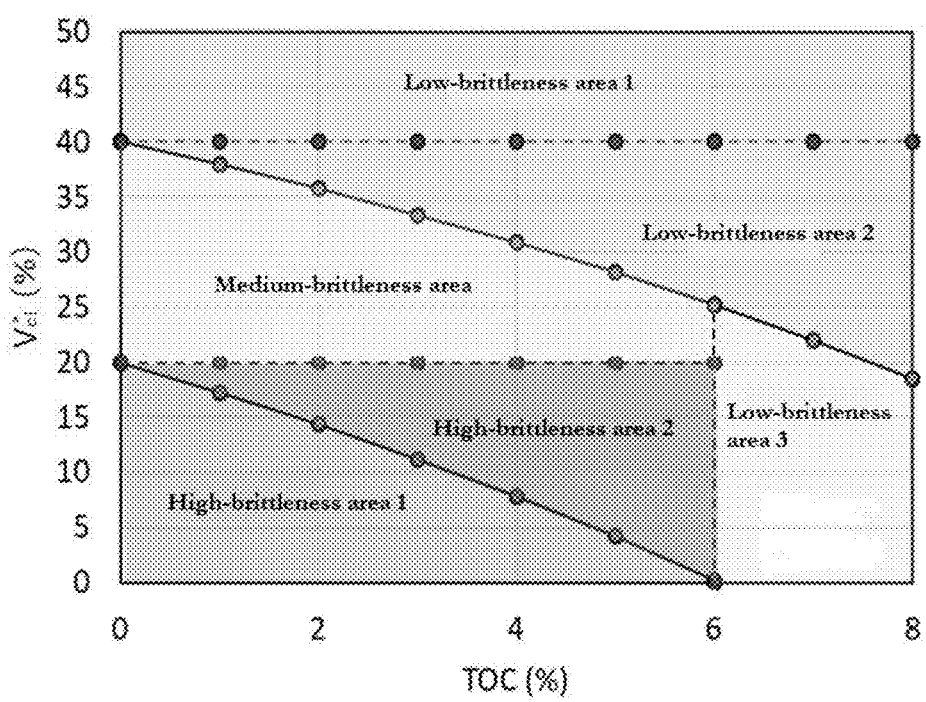
FIG. 2 is a shale brittleness grading chart in a shale brittleness sweet spot evaluation method according to an embodiment of the present invention.

As shown in FIG. 2, the chart is established by taking the shale total organic matter mass percent content as the abscissa and the shale clay volume percent content as the ordinate. The curve 1 and the curve 2 are marked in the chart. The $V_{cl}*$ of an area below the curve 1 is smaller than 20, and the shale brittleness index is greater than 80. The $V_{cl}*$ of an area between the curve 1 and the curve 2 is between 20 and 40, and the shale brittleness index is between 80 and 60. The $V_{cl}*$ of an area above the curve 2 is greater than 40, and the shale brittleness index is smaller than 60. The chart is further divided into a low-brittleness area 1, a low-brittleness area 2, a low-brittleness area 3, a medium-brittleness area, a high-brittleness area 1 and a high-brittleness area 2 in combination with the threshold of the TOC and the threshold of the $V_{cl}*$, thereby obtaining a final shale brittleness grading chart. The low-brittleness area 3 is determined according to TOC>6%. Statistic analysis shows that the higher the TOC is, the higher the lower limit value of $V_{cl}*$ is. When the TOC is greater than 6%, generally the $V_{cl}*$ is greater than 20%, i.e. when the $V_{cl}*$ is smaller than 60%, the total content of the TOC and the $V_{cl}*$ is generally greater than 40%.

The shale mineral volume percent content and the shale total organic matter mass percent content of the collected shale samples of the research area target interval can be detected by virtue of the shale brittleness grading chart, then the shale mineral volume percent content values and the shale total organic matter mass percent content values of the shale samples are substituted into the shale brittleness grading chart to obtain corresponding shale brittleness grades, so that the brittleness of the shale samples can be determined, and whether the shale samples are shale brittleness sweet spots or not can be determined.

Preferable embodiments of the present invention are described in detail above in conjunction with accompanying drawings. However, the present invention is not limited by details of the embodiments, technical solutions of the present invention can be subjected to multiple simple transformations within the technical conception scope of the present invention, and the simple transformations all fall into the protection scope of the present invention.

What needs to be additionally explained is that in case of no conflict, specific technical features described by above-mentioned specific embodiments can be combined in any appropriate mode, and to avoid unnecessary repeat, probable combination modes are not described additionally.

In addition, different embodiments of the present invention can also be arbitrarily combined, and should also be regarded as content disclosed by the present invention as long as ideas of the present invention are not obeyed.

The invention claimed is:

1. A method for exploring and fracturing a shale gas reservoir based on shale brittleness grade, comprising:
   collecting multiple shale samples from a research area target interval of the shale gas reservoir;
   measuring shale mineral volume percent content of the multiple shale samples by X-ray diffraction;
   measuring shale total organic matter mass percent content of the multiple shale samples by pyrolysis analysis;
   determining a brittleness evaluation formula of shale brittleness indexes, shale mineral volume percent content and shale total organic matter mass percent content according to a shale volume-mass conversion formula and a brittleness calculation formula containing the shale total organic matter volume percent content and the shale mineral volume percent content;
   drawing a shale brittleness grading chart of the research area target interval according to the brittleness evaluation formula and measured shale mineral volume percent content values and shale total organic matter mass percent content values of the multiple shale samples of the research area target interval; and
   determining shale brittleness grade corresponding to a shale sample of the research area target interval by finding, in the shale brittleness grading chart, a shale brittleness grade corresponding to a shale mineral volume percent content value and a shale total organic matter mass percent content values of the shale sample;
   determining a shale brittleness sweet spot for exploration and fracturing, when the shale brittleness grade corresponding to the shale sample is a predetermined grade, wherein the shale brittleness sweet spot corresponds to the shale sample,
   wherein fracturing effects and exploration capacities of the shale gas reservoir are improved through determining the shale brittleness sweet spot,
   wherein the shale volume-mass conversion formula is obtained as follows:

$\rho_K * V_K = \rho_{rock} * V_{rock}$ $V_K = \rho_{rock} * V_{rock} / \rho_o = 2.5 * V_{rock}$ wherein $\rho_K$ is a kerogen density, $\rho_K = 1.0$ g/cm³; $\rho_{rock}$ is a rock density, $\rho_{rock} = 2.5$ g/cm³; $V_K$ is kerogen volume percent content; $V_{rock}$ is rock volume percent content;

$V_O = k_0 V_K$ $V_O = 2.5 * k_0 V_{rock}$ wherein $V_O$ is volume percent content of total organic matter; $k_0$ is a conversion coefficient of kerogen converted into organic matter, and the shale volume-mass conversion formula is obtained by:

$V_O = 2.5 * k_0 TOC$ wherein TOC refers to the shale total organic matter mass percent content,
   wherein the conversion coefficient $k_0$ of the kerogen converted into the organic matter is 1.3.

2. The method according to claim 1, wherein the step of determining a brittleness evaluation formula of shale brittleness indexes, shale mineral volume percent content and shale total organic matter mass percent content according to a shale volume-mass conversion formula and the brittleness calculation formula containing the shale total organic matter volume percent content and the shale mineral volume percent content comprises:
   correcting the shale mineral volume percent content according to the shale total organic matter volume percent content; and
   substituting the corrected shale mineral volume percent content and the shale volume-mass conversion formula into the brittleness calculation formula containing the shale total organic matter volume percent content and the shale mineral volume percent content, thereby obtaining the brittleness evaluation formula.

3. The method according to claim 2, wherein the shale mineral volume percent content is corrected as follows:

$$V^*_{mineral} = \frac{V_{mineral}}{V_{qa} + V_{fe} + V_{ca} + V_{do} + V_{an} + V_{cl} + V_o}$$

wherein $V_{mineral}$ is uncorrected shale mineral volume percent content; $V^*_{mineral}$ is corrected shale mineral volume percent content; $V_{qa}$ is uncorrected shale quartz volume percent content; $V_{fe}$ is uncorrected shale feldspar volume percent content; $V_{ca}$ is uncorrected shale calcite volume percent content; $V_{do}$ is uncorrected shale dolomite volume percent content; $V_{an}$ is uncorrected shale analcite volume percent content; $V_{cl}$ is uncorrected shale clay volume percent content; and $V_o$ is the shale total organic matter volume percent content.

4. The method according to claim 3, wherein the step of drawing a shale brittleness grading chart of a research area target interval according to the brittleness evaluation formula and measured shale mineral volume percent content values and shale total organic matter mass percent content values of multiple shale samples of the research area target interval comprises:
   simplifying the brittleness evaluation formula to obtain a brittleness simplified formula of the shale brittleness indexes, the shale clay volume percent content and the shale total organic matter mass percent content; and
   drawing the brittleness grading chart according to the brittleness simplified formula, the shale mineral volume percent content values and the shale total organic matter mass percent content values.

5. The method according to claim 4, wherein the step of simplifying the brittleness evaluation formula to obtain the brittleness simplified formula of the shale brittleness indexes, the shale clay volume percent content and the shale total organic matter mass percent content comprises:
   simplifying the brittleness evaluation formula by approximately considering the sum of the volume of quartz, feldspar, calcite, dolomite, analcite, clay and total organic matter in shale as the volume of the shale, thereby obtaining the brittleness simplified formula.

6. The method according to claim 5, wherein the step of drawing the brittleness grading chart according to the brittleness simplified formula, the shale mineral volume percent content values and the shale total organic matter mass percent content values comprises:

drawing a correlation analysis diagram of the shale brittleness indexes and the shale clay volume percent content and a correlation analysis diagram of the shale brittleness indexes and the shale total organic matter mass percent content respectively according to the brittleness simplified formula, the shale total organic matter mass percent content values and the shale clay volume percent content value of the shale mineral volume percent content values;

determining a threshold of the shale clay volume percent content and a threshold of the shale total organic matter mass percent content according to the correlation analysis diagram of the shale brittleness indexes and the shale clay volume percent content, the correlation analysis diagram of the shale brittleness indexes and the shale total organic matter mass percent content, and given shale brittleness indexes;

determining a relationship curve of the shale total organic matter mass percent content and the shale clay volume percent content according to the given shale brittleness indexes and the brittleness simplified formula; and drawing the brittleness grading chart according to the relationship curve of the shale total organic matter mass percent content and the shale clay volume percent content, the threshold of the shale clay volume percent content and the threshold of the shale total organic matter mass percent content.

* * * * *